(12) United States Patent
Lu

(10) Patent No.: US 10,190,032 B2
(45) Date of Patent: Jan. 29, 2019

(54) VISCOELASTIC SURFACTANTS IN MIXED BRINES

(75) Inventor: Shaohua Lu, Katy, TX (US)

(73) Assignee: M-I L.L.C., Houston, TX (US)

( * ) Notice: Subject to any disclaimer, the term of this patent is extended or adjusted under 35 U.S.C. 154(b) by 897 days.

(21) Appl. No.: 14/410,084

(22) PCT Filed: Jun. 21, 2012

(86) PCT No.: PCT/US2012/043468
§ 371 (c)(1),
(2), (4) Date: Dec. 4, 2015

(87) PCT Pub. No.: WO2013/191695
PCT Pub. Date: Dec. 27, 2013

(65) Prior Publication Data
US 2016/0108303 A1    Apr. 21, 2016

(51) Int. Cl.
| | | |
|---|---|---|
| *E21B 43/22* | (2006.01) | |
| *C09K 8/68* | (2006.01) | |
| *C09K 8/035* | (2006.01) | |
| *C09K 8/504* | (2006.01) | |
| *C09K 8/506* | (2006.01) | |
| *E21B 36/00* | (2006.01) | |
| *E21B 21/00* | (2006.01) | |
| *C09K 8/40* | (2006.01) | |
| *E21B 43/04* | (2006.01) | |

(Continued)

(52) U.S. Cl.
CPC ............ *C09K 8/035* (2013.01); *C09K 8/40* (2013.01); *C09K 8/506* (2013.01); *C09K 8/5045* (2013.01); *C09K 8/68* (2013.01); *E21B 21/003* (2013.01); *E21B 36/003* (2013.01); *E21B 43/04* (2013.01); *E21B 43/16* (2013.01); *G01N 33/26* (2013.01); *C09K 2208/30* (2013.01)

(58) Field of Classification Search
CPC ...... C09K 8/68; C09K 2208/30; C09K 8/506; C09K 8/52; C09K 2208/26; C09K 8/12; E21B 21/003; E21B 43/04; E21B 43/16; E21B 33/138; E21B 36/003
See application file for complete search history.

(56) References Cited

U.S. PATENT DOCUMENTS

| | | |
|---|---|---|
| 4,662,448 A | 5/1987 | Ashford et al. |
| 5,979,557 A | 11/1999 | Card et al. |
| 6,239,183 B1 | 5/2001 | Farmer et al. |

(Continued)

FOREIGN PATENT DOCUMENTS

| | | |
|---|---|---|
| WO | 02/24831 A2 | 3/2002 |
| WO | 2007/063317 A1 | 6/2007 |

OTHER PUBLICATIONS

International Search Report and Written Opinion for corresponding PCT Application Serial No. PCT/US2012/043468, 13 pages.

*Primary Examiner* — Zakiya W Bates
(74) *Attorney, Agent, or Firm* — David J. Smith (57) ABSTRACT

Wellbore fluids may include at least one viscoelastic surfactant, a first brine solution including one or more water soluble monovalent cation salts, and a second brine solution including one or more water soluble divalent cation salts in an amount effective to increase the viscosity of the wellbore fluid. The wellbore fluid may be injected into a wellbore as a gravel packing agent, to enhance the thermal insulation of a production tubing or transfer pipe surrounded by at least one annuli, or to reduce fluid loss.

21 Claims, 2 Drawing Sheets

Schematic representation of the packing parameter, P (51) Int. Cl.
*E21B 43/16* (2006.01)
*G01N 33/26* (2006.01)

(56) References Cited

U.S. PATENT DOCUMENTS

| | | |
|---|---|---|
| 6,258,859 B1 | 7/2001 | Dahayanake et al. |
| 6,325,149 B1 | 12/2001 | Dobson, Jr. et al. |
| 6,367,548 B1 | 4/2002 | Purvis et al. |
| 6,435,277 B1 | 8/2002 | Qu et al. |
| 6,506,710 B1 | 1/2003 | Hoey et al. |
| 6,703,352 B2 | 3/2004 | Dahayanake et al. |
| 6,763,888 B1 | 7/2004 | Harris et al. |
| 6,790,812 B2 | 9/2004 | Halliday et al. |
| 7,060,661 B2 | 6/2006 | Dobson, Sr. et al. |
| 7,084,095 B2 | 8/2006 | Lee et al. |
| 7,148,185 B2 | 12/2006 | Fu et al. |
| 7,303,018 B2 | 12/2007 | Cawiezel et al. |
| 7,510,009 B2 | 3/2009 | Cawiezel et al. |
| 2006/0157248 A1 | 7/2006 | Hoefer et al. |
| 2008/0200353 A1 | 8/2008 | Dahayanake et al. |
| 2008/0202744 A1 | 8/2008 | Crews et al. |

Fig. 1 Schematic embodiment of molecular assembly of VES surfactant in micelles

Fig. 2 Schematic representation of the packing parameter, P

Fig. 3 Schematic representation of various packing parameters of VES

Fig. 4 : Gel strength and Tau Zero for Examples 1-5

VISCOELASTIC SURFACTANTS IN MIXED BRINES

FIELD

Embodiments disclosed herein relate generally to methods of injecting a wellbore fluid into a wellbore. In particular, embodiments disclosed herein relate generally to viscoelastic wellbore fluid systems incorporating mixed brines.

BACKGROUND

During the drilling of a wellbore, various fluids are typically used in the well for a variety of functions. The fluids may be circulated through a drill pipe and drill bit into the wellbore, and then may subsequently flow upward through wellbore to the surface. During this circulation, a wellbore fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

Another wellbore fluid used in the wellbore following the drilling operation is a completion fluid. Completion fluids broadly refer any fluid pumped down a well after drilling operations have been completed, including fluids introduced during acidizing, perforating, fracturing, workover operations, etc. A drill-in fluid is a specific type of wellbore fluid that is designed to drill and complete the reservoir section of a well in an open hole, i.e., the "producing" part of the formation. Such fluids are designed to balance the needs of the reservoir with drilling and completion processes. In particular, it is desirable to protect the formation from damage and fluid loss, and not impede future production. Most drill-in fluids contain several solid materials including viscosifiers, drill solids, and additives used as bridging agents to prevent lost circulation and as barite weighting material to control pressure formation.

A further application for wellbore fluids include annular fluids or packer fluids which are pumped into an annular opening between a casing and a wellbore wall or between adjacent, concentric strings of pipe extending into a wellbore. In the completion of oil and gas wells, it is currently the practice to place aqueous or non-aqueous hydrocarbon based fluids, known as packer fluids, into a casing annulus above a packer, specifically where the packer has been set to isolate production fluid from the casing annulus. Packer fluids, introduced into the casing annulus, fill the annular column to surface. Packer fluids are used to provide both pressure stability and thermal protection to the casing annulus of production oil and gas wells as well as in injection wells. The main function of a packer fluid related to pressure stabilization is to provide hydrostatic pressure in order to equalize pressure relative to the formation, to lower pressures across sealing elements or packers; or to limit differential pressure acting on the well bore, casing and production tubing to prevent collapse of the wellbore.

Wellbore fluid compositions are known to be flowable systems that are generally thickened to a limited extent. In many cases, wellbore fluids may include thickening agents such as polymers or viscoelastic surfactants, which serve to control the viscosity of the fluids. To obtain the fluid characteristics required to meet these challenges, the fluid may be easy to pump so only a small amount of pressure is required to force it through restrictions in the circulating fluid system, such as bit nozzles, down-hole tools, or narrow wellbore annuli. In other words, the fluid may have the lowest possible viscosity under high shear conditions. Conversely, in zones of the well where the area for fluid flow is large and the velocity of the fluid is slow or where there are low shear conditions, the viscosity of the fluid may be great enough to suspend and transport the drilled cuttings. The need for a sufficient viscosity also applies to the periods when the fluid is left static in the hole, where both cuttings and weighting materials need to be kept suspended to prevent settlement.

Viscoelastic surfactants are commonly used as thickening agents. Viscoelastic surfactants may be relatively small molecules with each molecule being less than 500 grams per mole (i.e., molecular weight less than 500). The individual molecules of surfactant begin to associate to form rod-like or spiraling-cylinder-like micelles or other micellar structures. These micelle structures are always in an equilibrium state of breaking and reforming. As dynamic structures, micelles are readily destroyed by shear, presence of hydrocarbons or increased temperature. While these features are desirable especially in a hydrocarbon-bearing formation, there is minimal control over the conditions under which micelle breakup occurs. Therefore, under conditions of exposure to oil, high temperature, high shear, or other "stress conditions", the viscoelastic surfactants rapidly return to their original small independent spherical micellar state. When the viscoelastic micelles are broken down to this small independent spherical micellar state, the desired viscous nature of the well fluid is lost. In some cases the loss is temporary, in others the loss may be more permanent.

Accordingly, there exists a continuing need to improve viscosification of wellbore fluids using viscoelastic surfactant compositions.

SUMMARY

In one aspect, embodiments disclosed herein relate to a method for injecting a fluid into a wellbore, the method includes injecting a wellbore fluid into the wellbore. The wellbore fluid includes at least one viscoelastic surfactant, a first brine solution including one or more water soluble monovalent cation salts, and a second brine solution including one or more water soluble divalent cation salts in an amount effective to increase the viscosity of the wellbore fluid.

In another aspect, embodiments disclosed herein relate to a method of finding of finding an optimal ratio of divalent brine to monovalent brine in a wellbore fluid including a viscoelastic surfactant. The method includes providing a mixture of viscoelastic surfactant and a monovalent brine, adding a divalent brine in incremental values, and measuring the rheological properties.

In another aspect, embodiments disclosed herein relate to a method of gravel packing a hole in a subterranean formation including injecting into the hole a gravel pack composition including gravel and a carrier fluid. The carrier fluid includes at least one viscoelastic surfactant, a first brine solution including one or more water soluble monovalent cation salts, and a second brine solution including one or more water soluble divalent cation salts in an amount effective to increase the viscosity of the carrier fluid.

In another aspect, embodiments disclosed herein relate to a method for enhancing the thermal insulation of a production tubing or transfer pipe surrounded by at least one annuli including adding a wellbore fluid to at least one annuli and maintaining the wellbore fluid in contact with the annuli to at least partially immobilize the wellbore fluid. The wellbore fluid includes at least one viscoelastic surfactant, a first brine solution including one or more water soluble monovalent cation salts, and a second brine solution including one or more water soluble divalent cation salts in an amount effective to increase the viscosity of the wellbore fluid.

In another aspect, embodiments disclosed herein relate to a method for reducing fluid loss including pumping a selected amount of a fluid loss pill into a formation. The fluid loss pill includes at least one viscoelastic surfactant, a first brine solution including one or more water soluble monovalent cation salts, and a second brine solution including one or more water soluble divalent cation salts in an amount effective to increase the viscosity of the fluid loss pill.

Other aspects and advantages of the invention will be apparent from the following description and the appended claims.

DETAILED DESCRIPTION

Embodiments disclosed herein relate to wellbore fluids having viscoelastic surfactants therein (and methods of using such wellbore fluids) for various well operations. Particularly, embodiments of the present disclosure relate to viscoelastic wellbore fluids formulated with mixed brines. The viscoelastic wellbore fluids formulated with mixed brines may be used as, but not limited to, completion fluids, drill-in fluids, packer fluids, displacement fluids, fracturing fluids, or carrier fluids for gravel packing.

The term "viscoelastic" refers to those viscous fluids having elastic properties, i.e., the liquid at least partially returns to its original form when an applied stress is released. As mentioned above, the wellbore fluids of the present disclosure may be used in applications where viscoelastic surfactant (VES) based fluids are placed in the wellbore for a variety of applications discussed herein. In accordance with the present disclosure, a mixture of monovalent and divalent brines may be used in conjunction with a viscoelastic surfactant to result in an unexpected increase in the wellbore fluid's viscosity. Any type or combination of viscoelastic materials that can form micelles (spherulite, cylindrical, bilayer, or inverted micelle) in the presence of counter ions in aqueous solutions, thereby imparting viscosity to the fluid may be used in keeping with the principles of this disclosure. In a particular embodiment, cylindrical micelles may behave in solution phase that closely resembles that of a polymer, and may result in entanglement or interaction between micelle structures to result in a change in viscosity. However, in accordance with the present disclosure, the inventors have found a mechanism which is believed to affect the micelle structures formed and results in the most desirable viscosity increase without simply adding greater quantities of the viscoelastic surfactant.

Figure 1:
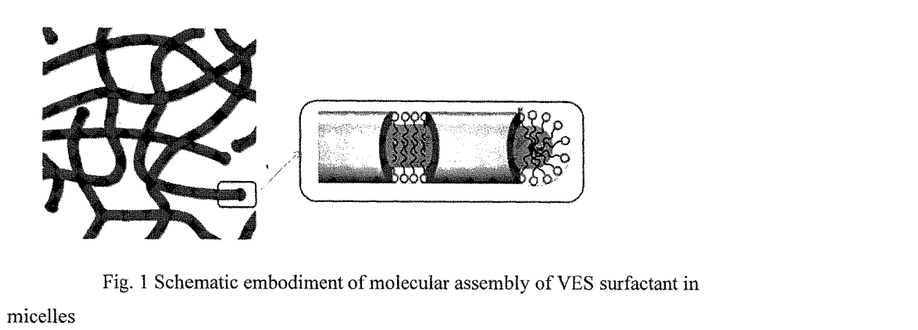
FIG. 1 is a schematic view of an embodiment of a molecular assembly of viscoelastic surfactant in micelles.
Figure 2:
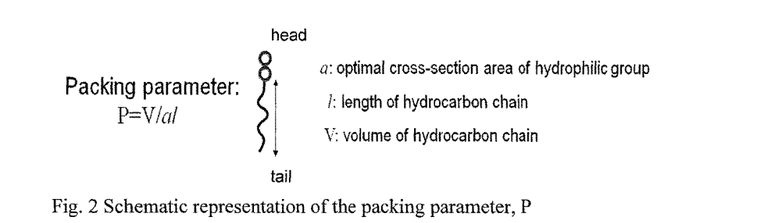
FIG. 2 is a schematic representation of a micellar structure for defining the packing parameter, P.

The high viscoelasticity of the VES fluids of the present disclosure may be attributed to worm-like or thread-like micelles that undergo entanglement and consequently form networks, as shown in FIG. 1. VES fluids are sometimes called a "living polymer." Rheological properties are determined by the micellar structure, which may be related to the geometry of the surfactant molecules as represented by the packing parameter and counter ions. A representative micellar structure is shown in FIG. 2, depicting a hydrophilic group at the top of the figure with a hydrocarbon chain extending therefrom. Based on the micellar structure, the packing parameter, P, may be defined as $P=V/al$, where V is the volume of the hydrocarbon chain, a is the optimal cross-sectional area of the hydrophilic group (sometimes referred to as headgroup) and l is the length of the hydrocarbon chain (sometimes referred to the tail). Without being bound to a particular theory, to achieve high viscosity, the surfactant molecules forming worm-like micelles should possess a low curvature that promotes one-dimensional growth or such effect may be achieved through the incorporation of a mixture of monvalent and divalent cations.

Figure 3:
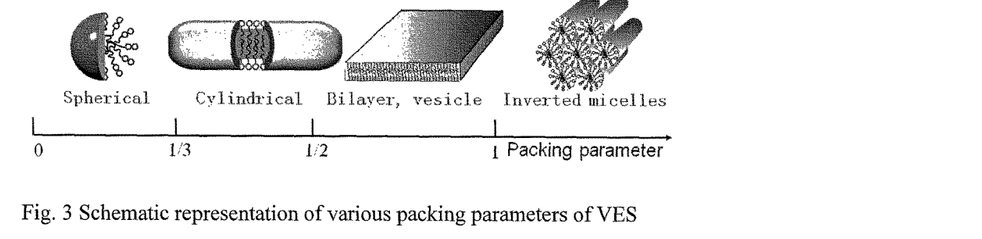
FIG. 3 is a schematic representation of embodiments of various packing parameters of viscoelastic surfactant.

The packing parameter may be used to estimate the aggregation structure (spherical, cylindrical, bilayer invert micelles) of the micelles. In turn, the aggregation structure can determine the viscosity or rheological property of the fluid. It is believed that cylindrical or worm-like micelles that undergo one dimensional growth may have the highest viscosity as compared to the other micellar structures. Therefore, various embodiments of the present disclosure seek to optimize the micellar structure to achieve maximum viscosity. As seen in FIG. 3, those surfactants that form cylindrical micelles may have a packing parameter around ½.

Common VES surfactants generally provide a constant v/l ratio, independent of tail length, of approximately 21 Å$^2$. Thus, assuming the chain length has no effect on the aggregation structure, the packing parameter and therefore viscosity is determined by the area of the headgroups. The area of headgroups may be influenced directly by the interaction between adjunct headgroups and other molecules (water and ions) in the wellbore fluid. Without being bound to a particular theory, the inventor of the present application believes that the presence of ions in solution affect the electrostatic force between charged headgroups, affecting the area of the headgroups and thus the packing parameter. Thus, for a given surfactant, having a given initial packing parameter, a mixture of monovalent and divalent cations (or anions, depending on the charge of the headgroup) may be used to adjust the packing parameter of the viscoelastic surfactant closer to the optimal ½ value. Specifically, the inventor of the present disclosure have found that a brine having a majority of its salts formed from monvalent salts and a minority (but necessarily present) amount of its salts formed from divalent salts will unexpectedly affect the viscosity of the fluid in a positive manner. Again, without being bound to a particular theory unless expressly stated in the claims, it is believed that the increase in viscosity is a result of this combination of monovalent salts and divalent salts' affect on the packing parameter. For example, for a zwitterionic surfactant having both positive and negative charges at the headgroup and a relatively high initial packing parameter, the divalent cations may increase the area of the headgroup and thus decrease the packing parameter. However, depending on the type (charge of the headgroup) and the native packing parameter of the surfactant, the type of ions incorporated may be altered depending on how the initial packing parameter should be adjusted to approach ½.

To provide the ionic strength for the desired micelle formation, the VES fluid systems of the present disclosure may include at least two water-soluble salts, at least one monvalent salt and at least one divalent salt. Adding such salts to the wellbore fluid may help promote micelle formation for the viscosification of the fluid. Suitable water-soluble salts may comprise lithium, ammonium, sodium, potassium, cesium, magnesium, calcium, or zinc cations, and chloride, bromide, iodide, nitrate, acetate, cyanate, or thiocyanate anions. Examples of suitable water-soluble salts that comprise the above-listed anions and cations include, but are not limited to, ammonium chloride, lithium bromide, lithium chloride, lithium nitrate, calcium bromide, calcium chloride, calcium nitrate, sodium bromide, sodium chloride, sodium nitrate, potassium chloride, potassium bromide, potassium nitrate, cesium nitrate, cesium chloride, cesium bromide, magnesium chloride, magnesium bromide, zinc chloride, and zinc bromide. The density of the brine may range from a lower limit of greater than 3 ppg, 5 ppg, 7 ppg, 9 ppg to an upper limit of less than 11 ppg, 13 ppg, 15 ppg, 17 ppg, 19 ppg, 20 ppg, where the density may range from any lower limit to any upper limit.

While many viscoelastic compositions are generally stated in the art to be usable with any aqueous fluids, including brines, the inventors of the present disclosure have found that better viscosity enhancement may be achieved by incorporating an amount of a divalent brine with a monovalent brine base fluid in which the viscoelastic surfactants are used.

Combinations of monovalent brines and divalent brines mixed with the VES may result in an unexpected viscosity increase. The achievable viscosity may be greater than either viscosity achievable with the monovalent brines or divalent brines mixed with the VES alone. An optimum mixing ratio may be determined based upon the packing parameter of the VES. Shear thinning and high Tau zero properties may be achieved when providing the mixture of monovalent and divalent brines providing advantages in certain wellbore fluid applications.

The presence of ions can suppress the electrostatic force between charged headgroups and thus reduces the area of head group. However, VES surfactants can have an initial packing parameter greater than the optimal value, ½, even without salt, as shown in the Table 1. It is believed that the combination of divalent and monovalent brines may lead to an optimized packing of the VES surfactants headgroups, similar to the packing of two different sizes of balls being better than the packing of single size balls. It may be theorized that the further the initial packing parameter of the VES is away from the optimal value, 0.5, more or less divalent ions may be necessary to effect the desired viscosity change.

Based on this theory, several viscoelastic surfactants were mixed with various ratios of monovalent and divalent brines, as shown in Table 1 below, and based on the Tau zero, gel strength and other rheological properties, optimal divalent/monvalent ratios were determined (molar ratio (%)=mol. divalent salt/mol. monovalent salt×100). The Tau zero, indicative of the resistance of the fluid to natural convection, and gel strength of the VES with mixed brines may be higher than VES mixed with either individual brine. VES-A a tallowalkylamidopropyl dimethylamine oxide surfactant, VES-B is a C18 betaine surfactant, and VES-C is a C22 betaine surfactant.

TABLE 1

|  | VES-A | VES-B | VES-C |
| --- | --- | --- | --- |
| Area of hydrophilic group, Å$^2$ | 12 | 28 | 28 |
| V/a, Å$^2$ | 21 | 21 | 21 |
| Initial packing parameter | 1.7 | 0.75 | 0.75 |
| Optimal divalent/monovalent molar ratio | 3~40% | 0.1~2% | 0.1~2% |

From this table it may be theorized that for a VES having an initial packing parameter up to 0.8 the ratio may be up to 2%, for 0.8 to 1.5 the ratio may be 1-10% and for 1.5 and higher the ratio may be 3% or more.

Thus, for any viscoelastic surfactant having an initial packing parameter, the optimal divalent/monovalent ratio may be estimated by mixing the surfactant in a monovalent brine and slowly adding a divalent brine therein to observe an increase in the Tau zero and/or gel strength of the fluid. In addition, a starting ratio of divalent to monovalent brine may be surmised based on the initial packing parameter compared to the packing parameters and optimal brine ratios shown in Table 1.

In one embodiment, the viscosity of the wellbore fluid may be controlled by increasing the amount of the divalent brine. In a particular embodiment, a brine may include halide or carboxylate salts of mono- and divalent cations of metals, such as cesium, potassium, calcium, zinc, and/or sodium. Further, when greater temperature stability is desired, one skilled in the art would appreciate that it may be desirable to include water miscible solvents such as various glycols to improve the thermal stability of the fluid system.

The wellbore fluids of the present disclosure may thus have several components: a monovalent salt, a divalent salt, and a viscoelastic surfactant. The monovalent salt and divalent salt may be dissolved in a base fluid, either aqueous or non-aqueous. Inventors of the present disclosure have found that wellbore fluids including both monovalent and divalent brines increase the viscosity of the fluid without large amounts of the divalent brine in the viscoelastic surfactant being used. Further, in a particular embodiment, the amounts of monovalent brine and divalent brine may be optimized to increase the viscosity while also maximizing/stabilizing the viscoelastic surfactants. It has been observed that upon the addition of the divalent brine, the viscosity change may be close to instantaneous.

The molar ratio of divalent to monovalent brines may be estimated based upon the packing parameter as shown above in Table 1. The farther away the packing parameter is from 0.5, the higher or lower the molar ratio of divalent to monovalent brines may be to effect the desired viscosity change (i.e., adding differing amounts of divalent ions or monovalent ions). For example, the molar ratio of divalent to monovalent salt may range from about 0.1% to about 40%, from about 0.1% to about 2%, from about 5% to about 25%, from about 4% to about 18%, or from about 0.2% to about 3%, depending on the particular surfactant (and its packing parameter) selected. To achieve these ratios, the amount of the first brine solution may range from about 70 to about 95 volume percent of the wellbore fluid and the amount of the second brine solution may range from about 0.1 to about 10 volume percent of the wellbore fluid. It is also within the scope of the disclosure that one or more of the salts may be added in solid rather than brine liquid form, if desired.

The inventor of the present disclosure has also found that a maximum viscosity is obtained at the optimal ratio of divalent brine to monovalent brine. It is theorized that at the optimum ratio of divalent brine to monovalent brine, the packing or assembly of the VES surfactants reaches an optimum structure, which leads to growth and entanglement of wormlike micelles and thus generates high viscosity. Ratios of divalent brine to monovalent brine over the optimum do not provide any advantages, and in fact, if the amount of divalent brine is increased too much, a reduction in the Tau zero and gel strength results. Thus, if a reduction in viscosity is desired, such as when breaking a gravel pack carrier fluid, an additional quantity of monovalent or divalent brine may cause a decrease in the fluid viscosity.

The viscoelastic surfactants used in the wellbore fluids of the present disclosure may include cationic, nonionic, anionic, amphoteric, and zwitterionic viscoelastic surfactant systems. In general, particularly suitable zwitterionic surfactants have the formula:

in which R is an alkyl group that contains from about 11 to about 23 carbon atoms which may be branched or straight chained and which may be saturated or unsaturated; a, b, a', and b' are each from 0 to 10 and m and m' are each from 0 to 13; a and b are each 1 or 2 if m is not 0, and (a+b) is from 2 to 10 if m is 0; a' and b' are each 1 or 2 when m' is not 0, and (a'+b') is from 1 to 5 if m is 0; (m+m') is from 0 to 14; and $CH_2CH_2O$ may also be $OCH_2CH_2$.

Preferred zwitterionic surfactants may include betaines. Two suitable examples of betaines are BET-O and BET-E. The surfactant in BET-O-30 is shown below; one chemical name is oleylamidopropyl betaine. It is designated BET-O-30 because as obtained from the supplier (Rhodia, Inc. Cranbury, N.J., U.S.A.) it is called Mirataine BET-O-30 because it contains an oleyl acid amide group (including a $C_{17}H_{33}$ alkene tail group) and contains about 30% active surfactant, the remainder being substantially water, sodium chloride, and propylene glycol. An analogous material, BET-E-40, is also available from Rhodia and contains an erucic acid amide group (including a $C_{21}H_{41}$ alkene tail group) and is approximately 40% active ingredient, with the remainder being substantially water, sodium chloride, and isopropanol. VES systems, in particular BET-E-40, optionally contain about 1% of a condensation product of a naphthalene sulfonic acid, for example sodium polynaphthalene sulfonate, as a rheology modifier, as described in U.S. Pat. No. 7,084,095, which is herein incorporated by reference. The surfactant in BET-E-40 is also shown below; one chemical name is erucylamidopropyl betaine. BET surfactants, and other VES's are described in U.S. Pat. No. 6,258,859, which is herein incorporated by reference. According to that patent, BET surfactants make viscoelastic gels when in the presence of certain organic acids, organic acid salts, or inorganic salts; in that patent, the inorganic salts are described as being present at a weight concentration up to about 30%. Co-surfactants may be useful in extending the brine tolerance, and to increase the gel strength and to reduce the shear sensitivity of the VES-fluid, in particular for BET-O-type surfactants. An example given in U.S. Pat. No. 6,258,859 is sodium dodecylbenzene sulfonate (SDBS). Still other suitable co-surfactants for BET-O-30 are certain chelating agents such as trisodium hydroxyethylethylenediamine triacetate.

Surfactant in BET-O-30 (when $n = 3$ and $p = 1$)

Surfactant in BET-E-40 (when $n = 3$ and $p = 1$)

Other betaines that are suitable include those in which the alkyl side chain (tail group) contains 11-23 carbon atoms (not counting the carbonyl carbon atom) which may be branched or straight chained and which may be saturated or unsaturated, n=2-10 (and n=3-5 in a more particular embodiment), and p=1-5 (and p=1-3 in a more particular embodiment), and mixtures of these compounds.

Exemplary cationic viscoelastic surfactants include the quaternary amine salts disclosed in U.S. Pat. Nos. 5,979, 557, and 6,435,277 which are hereby incorporated by reference. Examples of suitable cationic viscoelastic surfactants include cationic surfactants having the structure:

in which $R_1$ has from about 14 to about 26 carbon atoms and may be branched or straight chained, aromatic, saturated or unsaturated, and may contain a carbonyl, an amide, a retroamide, an imide, a urea, or an amine; $R_2$, $R_3$, and $R_4$ are each independently hydrogen or a $C_1$ to about $C_6$ aliphatic group which may be the same or different, branched or straight chained, saturated or unsaturated and one or more than one of which may be substituted with a group that renders the $R_2$, $R_3$, and $R_4$ group more hydrophilic; the $R_2$, $R_3$, and $R_4$ groups may be incorporated into a heterocyclic 5- or 6-member ring structure which includes the nitrogen atom; the $R_2$, $R_3$, and $R_4$ groups may be the same or different; $R_1$, $R_2$, $R_3$, and/or $R_4$ may contain one or more ethylene oxide and/or propylene oxide units; and $X^-$ is an anion. Mixtures of such compounds are also suitable. As a further example, $R_1$ is from about 18 to about 22 carbon atoms and may contain a carbonyl, an amide, or an amine, and $R_2$, $R_3$, and/or $R_4$ are the same as one another and contain from 1 to about 3 carbon atoms.

Cationic surfactants systems having the structure $R_1N^+(R_2)(R_3)(R_4)X^-$ may optionally contain the non-ionic amine analogs having the structure $R_1N(R_2)(R_3)$, incorporated therein. It is well known that commercially available cationic quaternary amine surfactants often contain the corresponding nonionic amines (in which $R_1$, $R_2$, and $R_3$ in the cationic surfactant and in the amine have the same structure). As received commercially available VES surfactant concentrate formulations, for example cationic VES surfactant formulations, may also optionally contain one or more members of the group consisting of alcohols, glycols, organic salts, chelating agents, solvents; mutual solvents, organic acids, organic acid salts, inorganic salts, oligomers, polymers, co-polymers, and mixtures of these members. They may also contain performance enhancers, such as viscosity enhancers, for example polysulfonates, for example polysulfonic acids, as described in U.S. Pat. No. 7,084,095 which is hereby incorporated by reference.

Another suitable cationic VES is erucyl bis(2-hydroxyethyl)methyl ammonium chloride, also known as (Z)-13 docosenyl-N—N-bis(2-hydroxyethyl)methyl ammonium chloride. It is commonly obtained from manufacturers as a mixture containing about 60 weight percent surfactant in a mixture of isopropanol, ethylene glycol, and water. Other suitable amine salts and quaternary amine salts include (either alone or in combination in accordance with the invention), erucyl trimethyl ammonium chloride; N-methyl-N,N-bis(2-hydroxyethyl) rapeseed ammonium chloride; oleyl methyl bis(hydroxyethyl) ammonium chloride; erucylamidopropyltrimethylamine chloride, octadecyl methyl bis (hydroxyethyl) ammonium bromide; octadecyl tris(hydroxyethyl) ammonium bromide; octadecyl dimethyl hydroxyethyl ammonium bromide; cetyl dimethyl hydroxyethyl ammonium bromide; cetyl methyl bis(hydroxyethyl) ammonium salicylate; cetyl methyl bis(hydroxyethyl) ammonium 3,4,-dichlorobenzoate; cetyl tris(hydroxyethyl) ammonium iodide; cosyl dimethyl hydroxyethyl ammonium bromide; cosyl methyl bis(hydroxyethyl) ammonium chloride; cosyl tris(hydroxyethyl) ammonium bromide; dicosyl dimethyl hydroxyethyl ammonium bromide; dicosyl methyl bis(hydroxyethyl) ammonium chloride; dicosyl tris(hydroxyethyl) ammonium bromide; hexadecyl ethyl bis(hydroxyethyl) ammonium chloride; hexadecyl isopropyl bis (hydroxyethyl) ammonium iodide; and cetylamino, N-octadecyl pyridinium chloride.

The viscoelastic surfactant system may also be based upon any suitable anionic surfactant. In some embodiments, the anionic surfactant is an alkyl sarcosinate. The alkyl sarcosinate can generally have any number of carbon atoms. Alkyl sarcosinates can have about 12 to about 24 carbon atoms. The alkyl sarcosinate can have about 14 to about 18 carbon atoms. Specific examples of the number of carbon atoms include 12, 14, 16, 18, 20, 22, and 24 carbon atoms. The anionic surfactant is represented by the chemical formula: $R_1CON(R_2)CH_2X$ wherein $R_1$ is a hydrophobic chain having about 12 to about 24 carbon atoms, $R_2$ is hydrogen, methyl, ethyl, propyl, or butyl, and X is carboxyl or sulfonyl. The hydrophobic chain can be an alkyl group, an alkenyl group, an alkylarylalkyl group, or an alkoxyalkyl group. Specific examples of the hydrophobic chain include a tetradecyl group, a hexadecyl group, an octadecentyl group, an octadecyl group, and a docosenoic group.

In some embodiments, to achieve the rheological properties desired for the fluids of the present disclosure, at least one amphoteric viscoelastic surfactant may be provided in the fluid. The term "amphoteric" refers to a compound that can act either as an acid or a base. Exemplary amphoteric viscoelastic surfactant systems include those described in U.S. Pat. No. 6,703,352, for example amine oxides. Other viscoelastic surfactant systems include those described in U.S. Pat. Nos. 6,239,183; 6,506,710; 7,060,661; 7,303,018; and 7,510,009, for example amidoamine oxides. These six references are hereby incorporated in their entirety. Mixtures of zwitterionic surfactants and amphoteric surfactants may also be suitable.

The selection of the surfactant concentration may depend on the particular wellbore operation (packer fluid, hydraulic fracturing, spacer fluid, drill-in fluid, etc). The amount of VES (in solvent) may range from about 1 to about 12 volume percent, or from about 2 to about 10 volume percent, or from about 4 to about 8 volume percent where the amount of surfactant in the solvent generally ranges from about 30 to 50 percent. These percentages are for VES which may be provided in a solvent. However, other amounts may be used, so long as the surfactant is present in an amount sufficient to impart the desired rheological effect by the formation of micelles within the wellbore fluid. In a particular embodiment, the amount of active surfactant may be selected based on the viscosity desired for the particular application. Further, while concentrations of greater than 10% may be used to generate a workable viscosity, the use of mixed brines may bring the packing parameter closer to 0.5 and encourage formation of cylindrical micelles, and may result in an increase or decrease in viscosity, and may reduce the amount of VES that is used in the fluid.

Based on this behavior, the present disclosure also relates to a method of designing an optimal range of brine mixtures to be used with viscoelastic surfactant(s) in a fluid such as a wellbore fluid. Specifically, an amount of viscoelastic surfactant may be mixed in a monovalent brine and incremental amounts of divalent brine (or divalent salts if a volume increase in the fluid is not desired) may be aliquoted into the monovalent brine/VES mixture. At each incremental addition, the rhological properties including Tau zero and gel strength may be taken and plotted. This may be continued until the Tau zero and/or gel strength properties return to approximately baseline (measured without any addition of divalent species). Further, the initial and incremental amount of divalent brine may be based on the packing parameter of the VES being used. For example, for a VES having a packing parameter closer to 0.5, smaller increments may be used, whereas larger increments may be used as the packing parameter increases substantially.

Conventional methods can be used to prepare the wellbore fluids disclosed herein in a manner analogous to those normally used, to prepare conventional water- and oil-based wellbore fluids. In one embodiment, a desired quantity of VES and a monovalent brine, as described above, are mixed together. Divalent brine may be added sequentially with continuous mixing either at the surface of the well or injected into the well after the VES and monovalent brine have been pumped down the well. In some embodiments, the VES may be incorporated into a premixed mixture of monovalent and divalent brines at the desired ratio, or the VES may be mixed with a divalent brine, and that mixture is subsequently added to a monovalent brine.

The wellbore fluids including VES fluids and a combination of brines (monovalent and divalent) may be used as a drill-in fluid, as a carrier fluid for gravel packing, as a spacer or displacement, or as a packer fluid.

For example, as a drill-in fluid the VES containing fluids of the present disclosure may be circulated down through a hollow drill stem and out through a drill bit attached thereto while rotating the drill stem to drill the wellbore. The drill-in fluid may be flowed back to the surface via the annular space between the drill string and the wellbore to deposit a filter cake on the walls of the wellbore and to carry drill cuttings to the surface.

In embodiments, the VES fluids of the present disclosure may be used as completion fluids, work-over fluids, spacer fluids, and liquid plugs. For example, as completion fluids, the VES fluids and combination of brines may be placed in the well annulus to facilitate final operations prior to initiation of production. The VES fluids of the present disclosure may be pumped through the wellbore, so that its fluid helps push other fluids through the annulus. In other embodiments, it may be pumped into the annulus above or below a packer element as a packer fluid, for example, to provide hydrostatic pressure to lower a differential pressure across the packer element and/or to provide differential pressure against a casing or formation wall to prevent well collapse. The VES fluids of the present disclosure may be used to control a well should downhole hardware lose integrity, without damaging the producing formation or completion components. The mixture of brines may be included in the VES prior to the fluid being placed downhole in a single stream embodiment.

Viscoelastic surfactant containing wellbore fluids, for example those used in the oilfield, may also contain agents that dissolve minerals and compounds, for example in formations, scale, and filtercakes. Such agents may be, for example, hydrochloric acid, formic acid, acetic acid, lactic acid, glycolic acid, sulfamic acid, malic acid, citric acid, tartaric acid, maleic acid, methylsulfamic acid, chloroacetic acid, aminopolycarboxylic acids, 3-hydroxypropionic acid, polyaminopolycarboxylic acids, for example trisodium hydroxyethylethylenediamine triacetate, and salts of these acids and mixtures of these acids and/or salts. For sandstone treatment, the fluid may also contain a hydrogen fluoride source. The hydrogen fluoride source may be HF itself or may be selected from ammonium fluoride and/or ammonium bifluoride or mixtures of the two; when strong acid is present the HF source may also be one or more of polyvinylammonium fluoride, polyvinylpyridinium fluoride, pyridinium fluoride, imidazolium fluoride, sodium tetrafluoroborate, ammonium tetrafluoroborate, and salts of hexafluoroantimony. When the formation-dissolving agent is a strong acid, the fluid may contain a corrosion inhibitor. The fluid optionally contains chelating agents for polyvalent cations, for example especially aluminum, calcium and iron (in which case the agents are often called iron sequestering agents) to prevent their precipitation. Some of the formation-dissolving agents just described are such chelating agents as well. Chelating agents are added at a concentration, for example, of about 0.5% (of active ingredient). When VES fluids contain strong acids, they may not be gelled and/or display low viscosity; when the pH increases as the acid reacts with the mineral, the system gels and the viscosity increases. Such fluids may be called viscoelastic diverting acids, or VDA's. The rheology enhancers may be used in viscoelastic surfactant fluid systems containing acids and chelating agents.

Other additives that may be included in the wellbore fluids disclosed herein include, for example, wetting agents, organophilic clays, viscosifiers, fluid loss control agents, surfactants, dispersants, interfacial tension reducers, pH buffers, mutual solvents, thinners, thinning agents, and cleaning agents. The addition of such agents should be well known to one of ordinary skill in the art of formulating wellbore fluids and muds.

When the VES containing fluids of the present disclosure are used as a gravel packing carrier fluid, a liner is provided with a cross-over sub assembly to allow a slurry of particulate material and the viscous fluid to be pumped through the liner and the cross-over sub assembly into the annulus of a lower wellbore section where the particulate material settles out of the slurry. The viscous fluid may then circulate back via the cross-over sub assembly and the annulus between the liner and the wellbore wall (or casing), to the surface. In order to be able to fill the annular space with sand completely and successfully, the hydrocarbon-bearing formation should have been previously covered with a thin layer of firm and substantially impermeable filter cake formed by the reservoir drilling fluid. This thin and impermeable filter cake may prevent the gravel pack fluid from entering the formation, and may result in gravel pack failure.

After the gravel pack sand has been successfully placed, the filter cake existing between the gravel pack sand and the formation needs to be removed before the flow of hydrocarbon is initiated. Without the removal of the filter cake, plugging of the production screen by the filter cake could occur, impairing production.

Various chemicals, breakers and mechanical devices have been developed and used to destroy a filter cake that is behind the gravel pack sand. Breakers are normally pumped on a separate trip after the gravel pack sand has been set. They are not pumped during the gravel pack operation because they can create precarious conditions for the operation. For instance, the acid-based breakers can destroy the filter cake during gravel pack operation, and consequently result in high fluid loss and premature failure in the gravel pack operation.

The wellbore fluid may be placed in the well prior to the emplacement of a fluid loss pill or diverting treatment and may result from a brine solution, including at least one viscoelastic surfactant and a first brine solution including one or more water soluble monovalent cation salts, being used as a drilling fluid or component of a drilling fluid used in the well. In embodiments, if fluid loss to the formation is detected, a monovalent brine solution (including the viscoelastic surfactant) may be injected into the well and into the area surrounding the fluid loss so that once the fluid loss pill or diverting treatment, including a divalent brine solution, is emplaced in the well, the monovalent brine and the diverting treatment may intereact to form a plug that may reduce the amount of fluid loss to the formation. A "plug" may be an obstructing mass of material. For example, if a well is originally drilled with a wellbore fluid including a viscoelastic surfactant and a monovalent brine and excessive fluid loss is encountered, then a divalent brine pill may be emplaced, to form the plug. In other embodiments, the wellbore fluid including at least one viscoelastic surfactant, a first brine solution including one or more water soluble monovalent cation salts, and a second brine solution including one or more water soluble divalent cation salts may be pre-mixed and injected into the well. The wellbore fluid may also be used as a fluid loss pill or diverting treatment.

The fluid loss pill or diverting treatment may be injected into a work string, flow to bottom of the wellbore, and then out of the work string and into the annulus between the work string and the casing or wellbore. This batch of treatment is typically referred to as a "pill." The pill may be pushed by injection of other completion fluids behind the pill to a position within the wellbore which is immediately above a portion of the formation where fluid loss is suspected. Injection of fluids into the wellbore is then stopped, and fluid loss will then move the pill toward the fluid loss location. Positioning the pill in a manner such as this is often referred to as "spotting" the pill. The fluid loss pill or diverting treatment may then react with the brine to form a plug near the wellbore surface, to reduce fluid flow into the formation.

The fluid loss pill or diverting treatment may be selectively emplaced in the wellbore, for example, by spotting the pill through a coil tube or by bullheading. A downhole anemometer or similar tool may be used to detect fluid flows downhole that indicate where fluid may be lost to the formation. The relative location of the fluid loss may be determined such as through the use of radioactive tags present along the pipe string. Various methods of emplacing a pill known in the art are discussed, for example, in U.S. Pat. Nos. 4,662,448, 6,325,149, 6,367,548, 6,790,812, 6,763,888, which are herein incorporated by reference in their entirety.

Accordingly, the wellbore fluid may also be used as an insulating medium such as a packer fluid to insulate or to help insulate the well tubing. In some embodiments, the the wellbore fluid of at least one viscoelastic surfactant and a first brine solution including one or more water soluble monovalent cation salts may be pumped into the annulus. The second brine solution including one or more water soluble divalent cation salts in an amount effective to increase the viscosity of the wellbore fluid, may be simultaneously or subsequently pumped down. The wellbore fluid may be added to an annuli or riser piping and maintained in contact with piping to at least partially immobilize the fluid. The wellbore fluid may therein serve as a packer providing insulation from outside conditions, such as cold water, permafrost, or high temperature formations.

Examples 1-18

Mixtures having a steady amount of VES with varying amounts of a monovalent brine and a divalent brine are shown in Table 2. Samples included the following components: VES-A, a tallowalkylamidopropyl dimethylamine oxide viscoelastic surfactant; NaBr (12.5 ppg); $CaBr_2$ (14.2 ppg) mixed in the various proportions. The samples were heat aged overnight at 150° F. The rheological properties were measured at 120° F. using a Fann 35 viscometer and are shown in Table 2 below.

Figure 4:
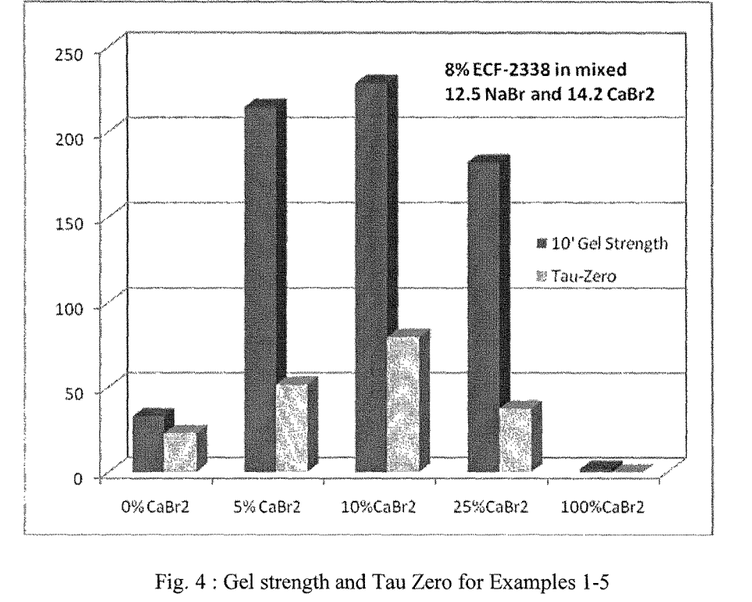
FIG. 4 is a graphic representation of gel strength and Tau zero for Examples 1-5.

As seen in FIG. 4, an optimum ratio of divalent brine to monovalent brine is achieved when the fluid properties are maximized. Subsequent amounts of divalent brine do not provide any improvement to the properties, and in fact, begin to degrade the properties.

TABLE 2

8% VES-A with NaBr (12.5 ppg) and $CaBr_2$ (14.2 ppg)

| | | Example # | | | | |
|---|---|---|---|---|---|---|
| | | 1 | 2 | 3 | 4 | 5 |
| VES-A | vol % | 8 | 8 | 8 | 8 | 8 |
| 12.5 ppg NaBr | vol % | 92 | 87.4 | 82.8 | 69.0 | 0.0 |
| 14.2 ppg $CaBr_2$ | vol % | 0 | 4.6 | 9.2 | 23.0 | 92.0 |
| $CaBr_2$:NaBr | mol:mol | 0:1 | 0.04:1 | 0.08:1 | 0.23:1 | 1:0 |
| RHEOLOGY | ° F. | 120 | 120 | 120 | 120 | 120 |
| 600 | | | 45 | 140 | 300 | 185 | 60 |
| 300 | | | 34 | 110 | 190 | 150 | 33 |
| 200 | | | 30 | 98 | 180 | 135 | 23 |
| 100 | | | 27 | 85 | 160 | 110 | 13 |
| 6 | | | 24 | 61 | 92 | 65 | 1 |
| 3 | | | 23 | 52 | 88 | 54 | 1 |
| GELS 10" | lbs/100 ft² | 30 | 167 | 197 | 166 | 3 |
| GELS 10' | lbs/100 ft² | 33 | 215 | 229 | 182 | 2 |
| GELS 30' | lbs/100 ft² | 35 | 215 | 220 | 195 | 2 |
| APPARENT VISC. | cP | 22.5 | 70 | 150 | 92.5 | 30 |
| PLASTIC VISC. | cP | 11 | 30 | 110 | 35 | 27 |
| YIELD POINT | lbs/100 ft² | 23 | 80 | 80 | 115 | 6 |
| Herschel-Bulkley model | n | 1 | 0.59 | 1 | 0.39 | 0.86 |
| | k | 0.02 | 1.48 | 0.22 | 10.47 | 0.16 |
| | Tau-Y | 24.54 | 55.12 | 85.36 | 40.08 | 0 |
| | Ro | 23 | 51.66 | 80 | 37.56 | 0 |

Mixtures having a steady amount of VES with varying amounts of a monovalent brine and a divalent brine are shown in Table 3. Samples included the following components: VES-A, a tallowalkylamidopropyl dimethylamine oxide viscoelastic surfactant; NaBr (12.5 ppg); $CaCl_2$ (11.6 ppg) mixed in the various proportions. The samples were heat aged overnight at 150° F. The rheological properties were measured at 120° F. using a Fann 35 viscometer and are shown in Table 3 below.

TABLE 3

8% VES-A with NaBr (12.5 ppg) and $CaCl_2$ (11.6 ppg)

| | | Example # | | |
|---|---|---|---|---|
| | | 6 | 7 | 8 |
| VES-A | vol % | 8 | 8 | 8 |
| 12.5 ppg NaBr | vol % | 92 | 82.8 | 0.0 |
| 11.6 ppg $CaCl_2$ | vol % | 0 | 9.2 | 92.0 |
| $CaCl_2$:NaBr | mol:mol | 0:1 | 0.09:1 | 1:0 |
| RHEOLOGY | ° F. | 120 | 120 | 120 |
| 600 | | 45 | 230 | 68 |
| 300 | | 34 | 186 | 52 |
| 200 | | 30 | 155 | 46 |
| 100 | | 27 | 135 | 37 |
| 6 | | 24 | 102 | 20 |
| 3 | | 23 | 94 | 16 |
| GELS 10" | lbs/100 ft² | 30 | 249 | 18 |
| GELS 10' | lbs/100 ft² | 33 | 150 | 17 |
| GELS 30' | lbs/100 ft² | 35 | 136 | |
| APPARENT VISC. | cP | 22.5 | 115 | 34 |
| PLASTIC VISC. | cP | 11 | 44 | 16 |
| YIELD POINT | lbs/100 ft² | 23 | 142 | 36 |
| Herschel-Bulkley model | n | 1 | 0.64 | 0.44 |
| | k | 0.02 | 1.66 | 2.64 |
| | Tau-Y | 24.54 | 98.9 | 12.7 |
| | Ro | 23 | 92.69 | 11.9 |

Mixtures having a steady amount of VES with varying amounts of a monovalent brine and a divalent brine are shown in Table 4. Samples included the following components: VES-A, a tallowalkylamidopropyl dimethylamine oxide viscoelastic surfactant; NaCl (10.0 ppg); $CaBr_2$ (14.2 ppg) mixed in the various proportions. The samples were heat aged overnight at 150° F. The rheological properties were measured at 120° F. using a Fann 35 viscometer and are shown in Table 4 below.

TABLE 4

8% VES-A with NaCl (10.0 ppg) and $CaBr_2$ (14.2 ppg)

| | | Example # | | |
|---|---|---|---|---|
| | | 9 | 10 | 11 |
| VES-A | vol % | 8 | 8 | 8 |
| 10.0 ppg NaCl | vol % | 92 | 82.8 | 0.0 |
| 14.2 ppg CaBr2 | vol % | 0 | 9.2 | 92.0 |
| $CaBr_2$:NaCl | mol:mol | 0:1 | 0.1:0 | 1:0 |
| RHEOLOGY | ° F. | 120 | 120 | 120 |
| 600 | | 155 | 185 | 60 |
| 300 | | 115 | 145 | 33 |
| 200 | | 105 | 128 | 23 |
| 100 | | 95 | 104 | 13 |
| 6 | | 56 | 67 | 1 |
| 3 | | 46 | 64 | 1 |
| GELS 10" | lbs/100 ft² | 149 | 152 | 3 |
| GELS 10' | lbs/100 ft² | 123 | >300 | 2 |
| GELS 30' | lbs/100 ft² | 85 | >300 | 2 |
| APPARENT VISC. | cP | 77.5 | 92.5 | 30 |
| PLASTIC VISC. | cP | 40 | 40 | 27 |
| YIELD POINT | lbs/100 ft² | 75 | 105 | 6 |

Mixtures having a steady amount of VES with varying amounts of a monovalent brine and a divalent brine are shown in Table 5. Samples included the following components: VES-A, a tallowalkylamidopropyl dimethylamine oxide viscoelastic surfactant; NaBr (10.3 ppg); $CaCl_2$ (9.9 ppg) mixed in the various proportions. The samples were heat aged overnight at 150° F. The rheological properties were measured at 120° F. using a Fann 35 viscometer and are shown in Table 5 below.

TABLE 5

4% VES-A with NaBr (10.3 ppg) and CaCl$_2$ (9.9 ppg)

| | | Example # | | | | | | |
|---|---|---|---|---|---|---|---|---|
| | | 12 | 13 | 14 | 15 | 16 | 17 | 18 |
| VES-A | vol % | 4 | 4 | 4 | 4 | 4 | 4 | 4 |
| 10.3 ppg NaBr | vol % | 96.0 | 86.4 | 72.0 | 48.0 | 24.0 | 9.6 | 0.0 |
| 9.9 ppg Cacl$_2$ | vol % | 0.0 | 9.6 | 24.0 | 48.0 | 72.0 | 86.4 | 96.0 |
| CaCl$_2$:NaBr | mol:mol | 0:1 | 0.09:1 | 0.25:1 | 0.75:1 | 1:0.43 | 1:0.15 | 1:0 |
| RHEOLOGY | ° F. | 120 | 120 | 120 | 120 | 120 | 120 | 120 |
| 600 | | 20 | 23 | 33 | 28 | 28 | 28 | 26 |
| 300 | | 15 | 16 | 22 | 24 | 18 | 20 | 20 |
| 200 | | 13 | 15 | 19 | 17 | 15 | 16 | 18 |
| 100 | | 11 | 11 | 13 | 14 | 12 | 11 | 14 |
| 6 | | 7 | 6 | 7 | 5 | 6 | 7 | 9 |
| 3 | | 6 | 5 | 5 | 4 | 5 | 6 | 7 |
| GELS 10" | lbs/100 ft$^2$ | 8 | 7 | 13 | 10 | 9 | 11 | 12 |
| GELS 10' | lbs/100 ft$^2$ | 7 | 18 | 25 | 22 | 20 | 16 | 13 |
| GELS 30' | lbs/100 ft$^2$ | | | | | | | |
| APPARENT VISC. | cP | 10 | 11.5 | 16.5 | 14 | 14 | 14 | 13 |
| PLASTIC VISC. | cP | 5 | 7 | 11 | 4 | 10 | 8 | 6 |
| YIELD POINT | lbs/100 ft$^2$ | 10 | 9 | 11 | 20 | 8 | 12 | 14 |
| Herschel-Bulkley | n | 0.62 | 0.70 | 0.72 | 0.40 | 0.82 | 0.63 | 0.53 |
| model | k | 0.19 | 0.14 | 0.19 | 1.72 | 0.07 | 0.29 | 0.52 |
| | Tau-Y | 6.22 | 5.24 | 5.48 | 0.72 | 5.43 | 5.83 | 6.94 |
| | Ro | 5.83 | 4.91 | 5.14 | 0.67 | 5.08 | 5.47 | 6.51 |

Examples 19-32

Mixtures having a steady amount of VES with varying amounts of a monovalent brine and a divalent brine are shown in Table 6. The samples included the following components: VES-B, an oleylamidopropyl betaine surfactant; NaBr (12.5 ppg); CaCl$_2$ (11.6 ppg) mixed in the various proportions. The samples were heat aged overnight at 150° F. The rheological properties were measured at 120° F. using a Fann 35 viscometer and are shown in Table 6 below.

TABLE 6

10% VES-B with NaBr (12.5 ppg) and CaCl$_2$ (11.6 ppg)

| | | Example # | | | | | | | |
|---|---|---|---|---|---|---|---|---|---|
| | | 19 | 20 | 21 | 22 | 23 | 24 | 25 | 26 |
| VES-B | vol % | 10 | 10 | 10 | 10 | 10 | 10 | 10 | 10 |
| 12.5 ppg NaBr | vol % | 90 | 89.9 | 89.5 | 89.1 | 88.2 | 85.5 | 84.6 | 0.0 |
| 11.6 CaCl2 | vol % | 0 | 0.1 | 0.5 | 0.9 | 1.8 | 4.5 | 5.4 | 90.0 |
| CaCl$_2$:NaBr | mol:mol | 0:1 | 0.001:1 | 0.004:1 | 0.008:1 | 0.015:1 | 0.04:1 | 0.05:1 | 1:0 |
| RHEOLOGY | ° F. | 120 | 120 | 120 | 120 | 120 | 120 | 120 | 120 |
| 600 | | | 45 | 46 | 40 | 83 | 190 | 150 | 12 | 45 |
| 300 | | 35 | 38 | 27 | 58 | 160 | 125 | 6 | 31 |
| 200 | | 32 | 34 | 23 | 42 | 150 | 120 | 4 | 24 |
| 100 | | 25 | 28 | 19 | 25 | 120 | 90 | 2 | 16 |
| 6 | | 10 | 14 | 16 | 23 | 37 | 30 | 2 | 3 |
| 3 | | 8 | 11 | 14 | 15 | 27 | 20 | 1 | 2 |
| GELS 10" | lbs/100 ft$^2$ | 8 | 14 | 32 | 69 | 159 | 53 | 1 | 2 |
| GELS 10' | lbs/100 ft$^2$ | 8 | 14 | 41 | 135 | 187 | 74 | 1 | 2 |
| GELS 30' | lbs/100 ft$^2$ | 8 | | | | | | | |
| APPARENT VISC. | cP | 22.5 | 23 | 20 | 41.5 | 95 | 75 | 6 | 15.5 |
| PLASTIC VISC. | cP | 10 | 8 | 13 | 25 | 30 | 25 | 6 | 7 |
| YIELD POINT | lbs/100 ft$^2$ | 25 | 30 | 14 | 33 | 130 | 100 | 0 | 17 |
| Herschel-Bulkley | n | 0.38 | 0.28 | 1 | 0.56 | 0.35 | 0.36 | 1 | 0.586 |
| model | k | 3.06 | 6.60 | 0.02 | 1.34 | 18.53 | 14.10 | 0.01 | 0.83 |
| | Tau-Y | 2.8 | 1.47 | 14.94 | 15.41 | 0 | 0 | 0 | 0 |
| | Ro | 2.6 | 1.38 | 14 | 14.44 | 0 | 0 | 0 | 0 |

Mixtures having a steady amount of VES with varying amounts of a monovalent brine and a divalent brine are shown in Table 7. The samples included the following components: VES-B, an oleylamidopropyl betaine surfactant; NaBr (12.5 ppg); CaBr$_2$ (14.2 ppg) mixed in the various proportions. The samples were heat aged overnight at 150° F. The rheological properties were measured at 120° F. using a Fann 35 viscometer and are shown in Table 7 below.

TABLE 7

10% VES-B with NaBr (12.5 ppg) and CaBr$_2$ (14.2 ppg)

| | | Example # | | | | | |
|---|---|---|---|---|---|---|---|
| | | 27 | 28 | 29 | 30 | 31 | 32 |
| VES-B | vol % | 10 | 10 | 10 | 10 | 10 | 10 |
| 12.5 ppg NaBr | vol % | 90 | 89.9 | 89.5 | 89.1 | 88.2 | 85.5 |
| 14.2 ppg CaBr2 | vol % | 0 | 0.1 | 0.5 | 0.9 | 1.8 | 4.5 |
| CaBr$_2$:NaBr | mol:mol | 0:1 | 0.001:1 | 0.004:1 | 0.007:1 | 0.015:1 | 0.04:1 |
| RHEOLOGY | ° F. | 120 | 120 | 120 | 120 | 120 | 120 |
| 600 | | 45 | 55 | 46 | 95 | 190 | 30 |
| 300 | | 35 | 38 | 35 | 58 | 165 | 15 |
| 200 | | 32 | 35 | 23 | 45 | 145 | 10 |
| 100 | | 25 | 25 | 18 | 33 | 115 | 6 |
| 6 | | 10 | 14 | 12 | 15 | 45 | 3 |
| 3 | | 8 | 10 | 9 | 12 | 33 | 2 |
| GELS 10" | lbs/100 ft$^2$ | 8 | 45 | 21 | 89 | 260 | 2 |
| GELS 10' | lbs/100 ft$^2$ | 8 | 95 | 49 | 260 | 245 | 2 |
| GELS 30' | lbs/100 ft$^2$ | 8 | 95 | 49 | | | |
| APPARENT VISC. | cP | 22.5 | 27.5 | 23 | 47.5 | 95 | 15 |
| PLASTIC VISC. | cP | 10 | 17 | 11 | 37 | 25 | 15 |
| YIELD POINT | lbs/100 ft$^2$ | 25 | 21 | 24 | 21 | 140 | 0 |
| Herschel-Bulkley | n | 0.38 | 0.69 | 0.47 | 0.85 | 0.32 | 0.89 |
| model | k | 3.06 | 0.39 | 1.61 | 0.23 | 22.52 | 0.05 |
| | Tau-Y | 2.8 | 11.07 | 6.91 | 12.99 | 0 | 2.11 |
| | Ro | 2.6 | 10.38 | 6.47 | 12.17 | 0 | 1.98 |

Embodiments of the present disclosure may provide one or more of the following advantages. Conventionally, requirements for wellbore fluids include high viscosity fluids which are sometimes achieved through use of viscoelastic surfactants. In such instances, viscosity of the fluid is increased by simply incorporating greater quantities of the surfactant. However, by using a mixture of brines, including a monovalent brine and a divalent brine with a viscoelastic surfactant, the viscosity of the wellbore fluid may be increased and the rheological properties optimized without increasing the amount of VES. Further, by using the combination of brines (monovalent and divalent) of the present disclosure, a quick response fluid may be formed. Furthermore, the fluids of the present disclosure may enhance hydraulics and lower the energy requirements of associated equipment. Further, the costs associated with high viscosity viscoelastic surfactants may be reduced.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for injecting a fluid into a wellbore, comprising:
   injecting a wellbore fluid into the wellbore, the wellbore fluid comprising:
      at least one viscoelastic surfactant;
      a first brine solution including one or more water soluble monovalent cation salts; and
      a second brine solution including one or more water soluble divalent cation salts in an amount effective to increase the viscosity of the wellbore fluid
   wherein the effective amount of water soluble divalent cation salts comprises a molar ratio of divalent cation salts to monovalent cation salts ranging from about 0.1 to about 40 percent.

2. The method of claim 1, wherein the viscoelastic surfactant is amphoteric or zwitterionic.

3. The method of claim 1, wherein the viscoelastic surfactant is a betaine surfactant.

4. The method of claim 3, wherein the betaine surfactant is oleylamidopropyl betaine surfactant.

5. The method of claim 3, wherein the effective amount of water soluble divalent cation salts comprises a molar ratio of divalent cation salts to monovalent cation salts ranging from about 0.1 to about 2 percent.

6. The method of claim 1, wherein the viscoelastic surfactant is an amidoamine oxide surfactant.

7. The method of claim 6, wherein the amidoamine oxide surfactant is a tallowalkylamidopropyl dimethylamine oxide surfactant.

8. The method of claim 6, wherein the effective amount of water soluble divalent cation salts comprises a molar ratio of divalent cation salts to monovalent cation salts ranging from about 3 to about 40 percent.

9. The method of claim 1, wherein injecting the wellbore fluid into the wellbore comprises injecting the wellbore fluid into an annular opening between a casing and a wellbore wall.

10. The method of claim 1, wherein injecting the wellbore fluid into the wellbore comprises injecting the wellbore fluid to drill and complete the reservoir section of a well in an open hole.

11. The method of claim 1, wherein injecting the wellbore fluid into the wellbore comprises injecting the wellbore fluid to control subsurface pressures.

12. The method of claim 1, wherein the wellbore fluid further comprises an additive selected from the group consisting of particulate material, wetting agents, organophilic clays, viscosifiers, fluid loss control agents, surfactants, dispersants, interfacial tension reducers, pH buffers, mutual solvents, thinners, thinning agents, cleaning agents, and combinations thereof.

13. The method of claim 1, wherein the amount of viscoelastic surfactant ranges from about 1 to about 12 volume percent of the wellbore fluid.

14. The method of claim 1, wherein the amount of the first brine solution ranges from about 70 to about 95 volume percent of the wellbore fluid.

15. The method of claim 1, wherein the amount of the second brine solution ranges from about 0.1 to about 10 volume percent of the wellbore fluid.

16. The method of claim 1, further comprising displacing the wellbore fluid comprising adjusting the viscosity of the wellbore fluid by adding additional water soluble divalent cation salts in an amount effective to decrease the viscosity of the wellbore fluid.

17. A method of finding of finding an optimal ratio of divalent brine to monovalent brine in a wellbore fluid including a viscoelastic surfactant, the method comprising:
    providing a mixture of viscoelastic surfactant and a monovalent brine;
    adding a divalent brine in incremental values, wherein the initial amount of divalent brine to be added is based upon a packing parameter of the viscoelastic surfactant; and
    measuring the rheological properties.

18. The method of claim 17, wherein the packing parameter is greater than 0.8.

19. A method of gravel packing a hole in a subterranean formation comprising:
    injecting into the hole a gravel pack composition comprising gravel and a carrier fluid, the carrier fluid comprising at least one viscoelastic surfactant; a first brine solution including one or more water soluble monovalent cation salts; and a second brine solution including one or more water soluble divalent cation salts in an amount effective to increase the viscosity of the carrier fluid, wherein the effective amount of water soluble divalent cation salts comprises a molar ratio of divalent cation salts to monovalent cation salts ranging from about 0.1 to about 40 percent.

20. A method for enhancing the thermal insulation of a production tubing or transfer pipe surrounded by at least one annuli comprising:
    (a) adding a wellbore fluid to at least one annuli; and
    (b) maintaining the wellbore fluid in contact with the annuli to at least partially immobilize the wellbore fluid,
        wherein the wellbore fluid comprises at least one viscoelastic surfactant; a first brine solution including one or more water soluble monovalent cation salts; and a second brine solution including one or more water soluble divalent cation salts in an amount effective to increase the viscosity of the wellbore fluid, wherein the effective amount of water soluble divalent cation salts comprises a molar ratio of divalent cation salts to monovalent cation salts ranging from about 0.1 to about 40 percent.

21. A method for reducing fluid loss, the method comprising:
    (a) pumping a selected amount of a fluid loss pill into a formation, the fluid loss pill comprising:
        (i) at least one viscoelastic surfactant;
        (ii) a first brine solution including one or more water soluble monovalent cation salts; and
        (iii) a second brine solution including one or more water soluble divalent cation salts in an amount effective to increase the viscosity of the fluid loss pill, wherein the effective amount of water soluble divalent cation salts comprises a molar ratio of divalent cation salts to monovalent cation salts ranging from about 0.1 to about 40 percent.

* * * * *